US012760278B2

(12) United States Patent
Jin

(10) Patent No.: US 12,760,278 B2

(45) Date of Patent: Oct. 13, 2026

(54) METHOD FOR OBTAINING ENDOMETRIAL MESENCHYMAL STEM CELLS FROM HUMAN MENSTRUAL BLOOD

(71) Applicant: SHANGHAI WOLWO STEM CELL TECHNOLOGY CO., LTD., Shanghai (CN)

(72) Inventor: Jin Jin, Shanghai (CN)

(73) Assignee: SHANGHAI WOLWO STEM CELL TECHNOLOGY CO., LTD., Shanghai (CN)

( * ) Notice: Subject to any disclaimer, the term of this patent is extended or adjusted under 35 U.S.C. 154(b) by 624 days.

(21) Appl. No.: 17/907,318

(22) PCT Filed: Apr. 2, 2021

(86) PCT No.: PCT/CN2021/085202

§ 371 (c)(1),
(2) Date: Sep. 26, 2022

(87) PCT Pub. No.: WO2021/197459

PCT Pub. Date: Oct. 7, 2021

(65) Prior Publication Data

US 2023/0116841 A1 Apr. 13, 2023

(30) Foreign Application Priority Data

Apr. 3, 2020 (CN) ........................ 202010259045.6

(51) Int. Cl.

*C12Q 1/24* (2006.01)
*C12N 5/0775* (2010.01)

(52) U.S. Cl.

CPC ............ *C12N 5/0665* (2013.01); *C12Q 1/24* (2013.01); *C12N 2500/90* (2013.01); *C12N 2509/00* (2013.01)

(58) Field of Classification Search

CPC ................................ C12N 5/0665; C12Q 1/24
See application file for complete search history.

(56) References Cited

U.S. PATENT DOCUMENTS

2023/0295577 A1* 9/2023 Hu ....................... C12N 5/0662

FOREIGN PATENT DOCUMENTS

| | | | |
|---|---|---|---|
| CN | 103966162 | A | 8/2014 |
| CN | 108034634 | A | 5/2018 |
| CN | 108998411 | A | 12/2018 |
| CN | 109182263 | A | 1/2019 |
| CN | 109845727 | A | 6/2019 |
| JP | 2010246476 | A | 11/2010 |
| JP | 2019512265 | A | 5/2019 |
| WO | 2020054755 | A | 3/2020 |

OTHER PUBLICATIONS

Musina et al. (2008) "Endometrial mesenchymal stem cells isolated from the menstrual blood" Bulletin of experimental biology and medicine, 145, 539-543. (Year: 2008).*

Mesh and Microns Sizes Chart and Information E-book, Industrial Specialties Mfg. and IS Med Specialties, version: Mar. 11, 2020, retrieved from: www.industrialspec.com/resources/mesh-and-micron-sizes/ (Year: 2020).*

Partial human-assisted machine translation of p. 10, lines 24-31, and p. 11, lines 1-15, of Chinese patent application CN202010691416.8, originally filed on Jul. 17, 2020. (Year: 2020).*

Masuda et al. (2016) "An improved method for isolation of epithelial and stromal cells from the human endometrium" Journal of Reproduction and Development, 62(2), 213-218. (Year: 2016).*

Osteen et al. (1989) "Development of a method to isolate and culture highly purified populations of stromal and epithelial cells from human endometrial biopsy specimens" Fertility and sterility, 52(6), 965-972. (Year: 1989).*

Du et al. (2016) "Endometrial mesenchymal stem cells isolated from menstrual blood by adherence" Stem Cells International, vol. 2016, Article ID 3573846, 8 pages. (Year: 2016).*

Ulrich et al. (2013) "Toward the use of endometrial and menstrual blood mesenchymal stem cells for cell-based therapies" Expert opinion on biological therapy, 13(10), 1387-1400. (Year: 2013).*

Notice of Reasons for Refusal issued for Japanese Patent Application No. 2022-558395, Dispatch Date: Aug. 15, 2023, 12 pages including English machine translation.

Zhou, Yf et al., "Isolation, culture and identification of menstrual blood-derived mesenchymal stem cells," Journal of Clinical Rehabilitative Tissue Engineering Research, Aug. 6, 2010, vol. 14, No. 32, pp. 5952-5956 (with English abstract).

International Search Report and Written Opinion issued for International Patent Application No. PCT/CN2021/085202, Date of mailing: Jul. 12, 2021, 8 pages including English translation.

Dong, R., "Isolation, Cultivation of Human Endometrial Stem/Progenitor Cells and Observation of Xenotransplantation Human Endometrial Cells," Medicine and Health Science, Chinese Master's Theses Full-text Database, No. 2, Feb. 15, 2015, ISSN: 1674-0246, 49 pages (with English abstract on pp. 3-4; cited in ISR).

Written Opinion issued for International Patent Application No. PCT/CN2021/085202, Date of mailing: Jul. 12, 2021, 5 pages including partial English translation.

(Continued)

*Primary Examiner* — James Joseph Graber
(74) *Attorney, Agent, or Firm* — HSML P.C.

(57) ABSTRACT

Provided are a method for obtaining endometrial mesenchymal stem cells from human menstrual blood and the endometrial mesenchymal stem cells prepared thereby. The method include: 1) subjecting an aliquot of menstrual blood to cascade filtration through graded cell strainers of decreasing mesh sizes to separate tissue debris, wherein said cell strainers include a filter-through cell strainer for collecting filtrate and a retention cell strainer for collecting retentate, wherein the mesh size of the retention cell strainer is smaller than that of the filter-through cell strainer; 2) collecting the retentate on the retention cell strainer as the tissue debris; 3) culturing the tissue debris in a mesenchymal stem cells medium; and 4) collecting adherent cells as the endometrial mesenchymal stem cells.

24 Claims, 2 Drawing Sheets

(56) References Cited

OTHER PUBLICATIONS

Extended European Search Report issued for European Patent Application No. 21778996.5, dated Apr. 8, 2024, 8 pages.
Sun, Y. et al., "High-yield isolation of menstrual blood-derived endometrial stem cells by direct red blood cell lysis treatment," Biology Open (2019) 8, 8 pages. (Cited in EESR).
Liu, Y. et al., "Biological characteristics of human menstrual blood-derived endometrial stem cells," J. Cell. Mol. Med. vol. 22, No. 3, 2018, p. 1627-1639. (Cited in EESR).

* cited by examiner

METHOD FOR OBTAINING ENDOMETRIAL MESENCHYMAL STEM CELLS FROM HUMAN MENSTRUAL BLOOD

FIELD OF THE INVENTION

This application pertains to the field of preparation of mesenchymal stem cells, and specifically a method of obtaining endometrial mesenchymal stem cells from human menstrual blood.

BACKGROUND

In recent years, mesenchymal stem cells (MSCs) are attracting extensive research attention for its robust proliferation capability, low immunogenicity, multipotency and lesion-targeted migration in tissues, among other advantageous features. Bone marrow-derived mesenchymal stem cells (BMSCs) are the first found mesenchymal stem cells, and also presently the most commonly used stem cells in clinical and research. However, challenges in supplies, like the bone marrow puncture under anesthesia and the significant decrease of autologous bone marrow stem cells with aging, hindered the clinic application of BMSCs. Human endometrium is highly dynamic, which periodically undergoes the phases of proliferation, secretion and menstruation. It's also highly regenerative, which can grow from 0.5-1 mm after menstruation to 5-7 mm in thickness. Female endometrium is highly regenerative, which may undergo 400 or more cycles of self-renewal, proliferation, differentiation and shedding in lifetime. Endometrium-derived mesenchymal stem cells can be found not only in the basal layer but also in the menstrual blood, which thus are resourcefully accessible. Therefore, human endometrial mesenchymal stem cells (hEMSCs) are getting more and more interests. Endometrial mesenchymal stem cells can be used as seed cells in various applications with promising utility, including, for example, cell therapy, tissue engineering and regenerative medicine.

At present, for separation of mesenchymal stem cells, mainly used are methods of tissue digestion and methods of gradient density centrifugation. Tissue digestion can obtain a large number of viable cells from living material in a short time, whereby the obtained cells exhibit properties close to in vivo performances, especially the growth profile, which make them particularly suitable for use in experiments and studies such as drug tests and cell differentiation. However, also apparent are the concerns and challenges in operability and the susceptibility to contamination. For example, inappropriate timing of digestion may directly impair purity and biological property of the primary harvest of mesenchymal stem cells, disrupt cell structure, interfere proliferation and differentiation, and may even result in a heterogeneous cell population. Meanwhile, digestion enzymes can be expensive and thus the experiment cost be inevitably raised. Gradient density centrifugation (also known as the "mononuclear method") separates different particles based on their differentia in density and size. Particles of different densities and sizes have different sedimentation rates in fluid, each settling at a distinct rate under a given centrifugal force, and can thereby be sorted by gravity and centrifugal force. Though the method is applicable for purification of mononuclear cells, it is not applicable for separating or purifying cells from tissues. Therefore, there exists the need for a method applicable for separation and purification of endometrial mesenchymal stem cells from human menstrual blood to facilitate the pharmaceutical development of EMSCs.

SUMMARY OF THE INVENTION

In a first aspect, provided is a method for obtaining endometrial mesenchymal stem cells from human menstrual blood, comprising:

1) subjecting an aliquot of menstrual blood to cascade filtration through graded cell strainers of decreasing mesh sizes to separate tissue debris, wherein said cell strainers include a filter-through cell strainer for collecting filtrate and a retention cell strainer for collecting retentate, wherein the mesh size of the retention cell strainer is smaller than that of the filter-through cell strainer;
2) collecting the retentate on the retention cell strainer as the tissue debris;
3) culturing the tissue debris in a mesenchymal stem cells medium; and
4) collecting adherent cells as the endometrial mesenchymal stem cells.

In some embodiments, said cascade filtration includes passing through at least three grades of cell strainers, preferably passing through at least four grades of cell strainers.

In some embodiments, said cascade filtration includes passing through one or two or more grades of filter-through cell strainers, and/or includes passing through one or two or more grades of retention cell strainers. Preferably, said cascade filtration includes two or more grades of retention cell strainers, and said step 2) of collecting the retentate on the retention cell strainer includes pooling the tissue debris retained on the multiple grades of retention cell strainers.

In some embodiments, said step 2) of collecting the retentate on the retention cell strainer includes releasing the tissue debris retained on the retention cell strainer(s) via back-flush with a washing fluid.

In some embodiments, said step 2) of collecting the retentate on the retention cell strainer further includes washing the tissue debris with a washing fluid.

In another aspect, provided is endometrial mesenchymal stem cells obtained by the method of the invention.

DETAILED DESCRIPTION OF THE INVENTION

Figure 1:
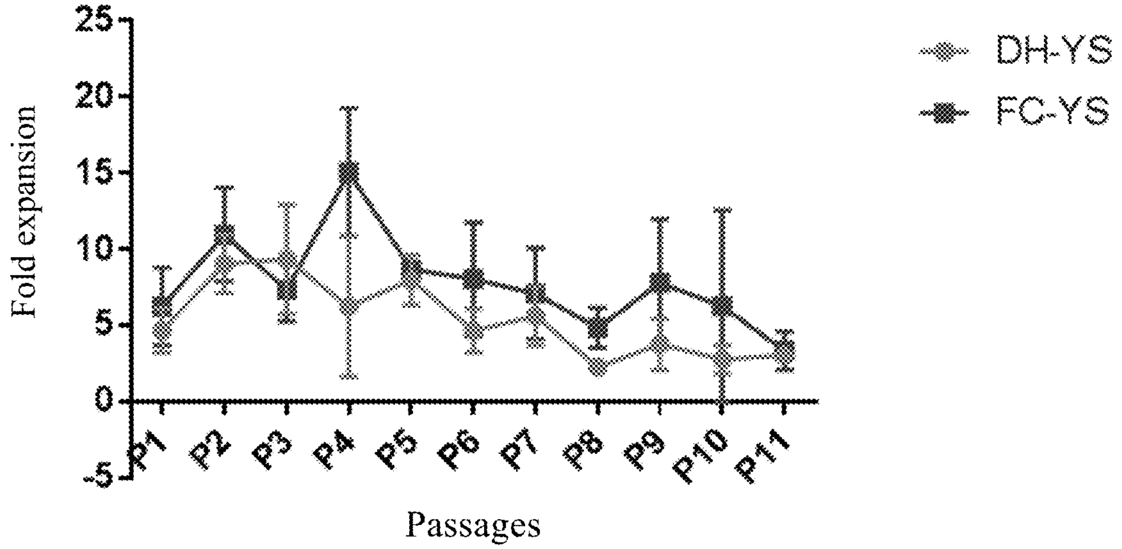
FIG. 1 shows fold expansion of EMSCs prepared by the mononuclear method and EMSCs prepared by the method of the invention in comparison.

In the present disclosure, components and preferred components can be recombined into alternative embodiments of the invention, unless otherwise specified expressively.

In the present disclosure, embodiments and preferred embodiments can be reorganized with one another into alternative embodiments of the invention, unless otherwise specified expressively.

In the present disclosure, features and preferred features can be recombined into alternative embodiments of the invention, unless otherwise specified expressively.

As used herein, "a" and "an" means "at least one", unless otherwise specified expressively.

In the present disclosure, ranges are each defined by a lower limit and an upper limit, wherein either limit may have more than one values of option. A given rang is defined in boundary by a selected lower limit and a selected upper limit, and all ranges defined thereby are inclusive and combinable to encompass ranges defined by anyone of the lower limits and anyone of the upper limits.

Specifically, in a first aspect, provided is a method for obtaining endometrial mesenchymal stem cells from human menstrual blood, comprising:

1) subjecting an aliquot of menstrual blood to cascade filtration through graded cell strainers of decreasing mesh sizes to separate tissue debris, wherein said cell strainers include a filter-through cell strainer for collecting filtrate and a retention cell strainer for collecting retentate, wherein the mesh size of the retention cell strainer is smaller than that of the filter-through cell strainer;
2) collecting the retentate on the retention cell strainer as the tissue debris;
3) culturing the tissue debris in a mesenchymal stem cells medium; and
4) collecting adherent cells as the endometrial mesenchymal stem cells.

In an embodiment, the method comprises the followings:

1) Tissue separation: subjecting an aliquot of menstrual blood to cascade filtration through graded cell strainers of decreasing mesh sizes;
2) Tissue back-flushing: releasing the tissue debris retained on cell strainer via back-flush with a washing fluid;
3) Tissue washing: resuspending and washing the tissue debris in the washing fluid, followed by centrifugation to recover the pellet of tissue debris;
4) Tissue culturing: resuspending the pellet of tissue debris into a suspension in culture medium, which was then inoculated into a culture flask, followed by addition of culture medium and culturing in an incubator;
5) Collecting adherent cells as endometrial mesenchymal stem cells.

In some embodiments, the collected endometrial mesenchymal stem cells may be further expanded.

For the present invention, the cell strainers may be of whatever a porous structure that is capable of separating particles based on differentia in size without contaminating the material such as tissues and cells. Cascade filtration is a process of sifting by passing through graded cell strainers of decreasing mesh sizes in sequence to obtain graded retentates of different size distributions, or graded filtrates of different size distributions.

In some embodiments of the invention, first, a filter-through cell strainer of larger mesh size is used to retain and remove oversize tissue debris, and then a retention cell strainer of smaller mesh size is used to retain and collect the tissue debris for culturing. In the present disclosure, the term "tissue debris" refers to tissues in the form of debris or fragments, with no intention to limit to a product of some specific means of disruption or fragmentation.

In some embodiments, a retention cell strainer may have a mesh size ranging from 70 mesh to 160 mesh, preferably from 80 mesh to 160 mesh. The present invention involves at least one grade of retention cell strainer, and optionally and preferably two or more grades of retention cell strainers of decreasing mesh sizes. When multiple grades of retention cell strainers were used, tissue debris retained by different grades of cell strainers can be pooled for use in subsequent steps. This may involve, for example, releasing the retained debris from the strainer via back-flush with a washing fluid followed by pooling the washes, or scraping and collecting the debris followed by resuspension, washing, etc.

In the present invention, a filter-through cell strainer is used to remove oversize tissue debris and to collect the filtrate. Preferably, tissue debris smaller than the mesh size of 30 mesh, 35 mesh, 40 mesh or even a lower mesh size can be collected thereby, and correspondingly, the filter-through cell strainers may include those having a mesh size not exceeding 30 mesh, 35 mesh or 40 mesh or a even lower mesh size. For example, to collect tissue debris smaller than the mesh size of 36 mesh, the filter-through cell strainer(s) may include at least a grade of cell strainer of 36 mesh. Oversize tissue debris may be removed using one or more grades of strainers. Accordingly, the present invention involves at least one grade of filter-through cell strainer, and optionally and preferably two or more grades of filter-through cell strainers of decreasing mesh sizes. A filter-through cell strainer may have a mesh size ranging from 18 mesh to 60 mesh, preferably 36 mesh to 60 mesh, more preferably 36 mesh to 50 mesh, and even more preferably 36 mesh to 40 mesh.

In some embodiments, the step of cascade filtration includes passing through at least three grades of cell strainers, preferably passing through at least four grades of cell strainers. For example, the step of cascade filtration may include passing through at least two grades of filter-through cell strainers and at least one grade of retention cell strainer, or passing through at least one grade of filter-through cell strainer and two grades of retention cell strainers, or passing through at least two grades of filter-through cell strainers and two grades of retention cell strainers.

Retained tissue debris can be released from a retention cell strainer by any of suitable methods as will be a selection of sound judgment by an artisan in the art, including but not limited to scraping, picking, and back-flush. In some embodiments, the tissue debris retained on a cell strainer was washed down by back-flush with a washing fluid. In the present disclosure, the terms "tissue back-flushing" and "back-flush" refer to the operation of flushing down the retentate from a strainer using a flow of washing fluid in the direction opposite to the flow of filtration through the cell strainer. For a maximum recovery of retentates, the endpoint of flushing may be set as disappearance of any tissues visible to the naked eye.

For example, said back-flush may include the following steps: collecting the cell strainer(s) with tissue debris retained thereon; placing one or more of the cell strainer(s) with tissue debris retained thereon in a culture dish, wherein the number of strainer(s) depends on the size of the dish (e.g., five at the most for a dish of 10 $cm^2$); adding into the culture dish washing fluid to just submerge the strainer(s) with tissue debris retained thereon; aspirating the washing fluid from the culture dish using a Pasteur pipette to wash the strainer(s) via back-flush to release the tissue debris retained thereon until there is no tissue visible to the naked eye on the strainer(s).

In some embodiments, the method of the invention may further include a step of washing to clean the tissue, i.e., the tissue debris harvested from the retention cell strainer(s), which may be, for example, resuspending the tissue debris in a washing fluid, optionally followed by solid-liquid separation (e.g., filtration or centrifugation) to obtain the pellet of washed (i.e., cleaned) tissue debris. For instance, when tissue debris is harvested from the strainer(s) by means of back-flush, tissue washing may include collecting the washes from the back-flush, collecting the pellet of tissue debris by means of solid-liquid separation (e.g., filtration or centrifugation, with the supernatant being discarded) and adding washing fluid to the pellet, wherein the specified steps may be repeated to obtain a pellet of washed and cleaned tissue debris. For centrifugation, it may be at the force of 400 g for 10 minutes at 20-22° C., preferably 20° C.

For the present invention, the "washing fluid" may be a buffer that is conventionally used in cell manipulation, such as a phosphate buffer-based washing fluid. The washing fluid may include one or more supplements as needed, such as an antibiotic. In some embodiments of the invention, the washing fluid is a phosphate buffer, and preferably a phosphate buffer comprising an antibiotic. Preferably, the antibiotic may be selected from the group consisting of Gentamicin, Penicillin, Streptomycin, Amphotericin B, or a combination thereof. Preferably, in the washing fluid, if present, the concentration of Gentamicin may be 50-100 U/mL, preferably 100 U/mL; if present, the concentration of Penicillin may be 180-200 U/mL, preferably 200 U/mL; if present, the concentration of Streptomycin may be 0.15-0.2 mg/mL, preferably 0.2 mg/mL; if present, the concentration of Amphotericin B may be 4-5 μg/mL, preferably 5 μg/mL.

In the step 3) culturing the tissue debris in a mesenchymal stem cells medium, i.e., "tissue culturing", wherein the tissue debris was cultured in a mesenchymal stem cell medium, the tissue debris is inoculated into the mesenchymal stem cell medium and cultured under a condition such that adherent mesenchymal stem cells grow from the tissue debris. In some embodiments, the step of inoculation may include resuspending the pellet of tissue debris into a suspension in the mesenchymal stem cell medium for inoculation. The tissue may be cultured in a culture flask. Optionally, after ensuring that the endometrial mesenchymal stem cells are tightly adhered to the vessel wall (e.g., after tissue-culturing for 48 hours), there may be included a step of removing non-adherent contaminant cells (e.g., erythrocytes) to preclude contamination. The culturing may then be continued, and the culture is ready for passaging when reaching 90%-100% confluence.

The present invention has no limits on usable mesenchymal stem cell medium. It may be any culture medium that is known as applicable to mesenchymal stem cells, and it may be either purchased or in-house prepared. Examples of mesenchymal stem cell medium include the primary MSC serum-free medium available from Beijing Youkang Technology Co., Ltd and the Amniocyte Culture Medium available from Guangzhou Baiyunshan Baidi Biopharmaceutical Co., Ltd.

In some embodiments, the tissue is cultured under a condition typical for mesenchymal stem cell culturing, such as at 5% $CO_2$, 37° C. The culturing may last for 4-6 days, preferably 5 days.

In some embodiments, the method may further include, after said tissue culturing, a step of separating the adherent endometrial mesenchymal stem cells for expansion, and optionally a step of expansion.

In some embodiments, there may be optionally included before step 1) an examination on the collected menstrual blood for contamination. Specifically, a sample of the collected menstrual blood is mixed with a washing fluid, preferably a phosphate buffer comprising an antibiotic, such as a phosphate buffer comprising Gentamicin and Amphotericin B; an aliquot of the mixture is added into the culture medium and incubated in an incubator; and the culture is monitored for contamination. Therein, the sample of menstrual blood may be mixed with the washing fluid at the ratio of 1:1.

In another aspect, provided is endometrial mesenchymal stem cells prepared by the method of the invention. The endometrial mesenchymal stem cells obtained thereby advantageously have increased proliferation rate and fold expansion in passaging as well as desirable differentiate potentials, compared with those prepared by prior art techniques such as the mononuclear method.

EXAMPLES

The present invention will be further described in details with reference to the examples below. It should be understood that these examples are merely provided for the purpose of illustration, with no intention to limit the scope of the invention in any sense.

Example 1: Preparation of Endometrial Mesenchymal Stem Cells

Endometrial mesenchymal stem cells were prepared according to the method of the invention. The process is detailed as follows:

I. Tissue Separation:

Menstrual blood in a 50 mL spin tube was sequentially filtered through an 18 mesh stainless cell strainer, a 36 mesh stainless cell strainer, an 80 mesh stainless cell strainer and a 160 mesh stainless cell strainer.

II. Tissue Back-Flushing:

1) The 80 mesh and the 160 mesh stainless cell strainers though which the menstrual blood was passed through in step I were placed in 10 $cm^2$ culture dishes, 5 strainers per dish at the most. To each 10 $cm^2$ culture dish, 40 mL washing fluid was added to just submerge the strainers with tissue debris retained thereon, wherein the washing fluid was phosphate buffer containing 100 U/mL Gentamicin and 5 μg/mL Amphotericin B;
2) The tissue debris retained on the 80 mesh and the 160 mesh cell strainers were released via back-flush with the washing fluid in the culture dish using a 3 mL Pasteur pipette.

III. Tissue Washing:

1) After the back-flush, the obtained washes comprising the tissue debris were collected into 50 mL spin tubes, 40 mL per tube, and centrifuged at 400 g, 20° C., for 10 minutes, the supernatant being discarded then;
2) To each spin tube, 10 mL washing fluid was added using a pipette to resuspend the pellet; the resuspensions were pooled in a 50 mL spin tube, centrifuged at 400 g, 20° C., for 10 minutes, the supernatant being discarded then;
3) To the spin tube, 30 mL washing fluid was added using a pipette to resuspend the pellet; the resuspension was centrifuged at 400 g, 20° C., for 10 minutes, the supernatant being discarded then.

Figure 2:
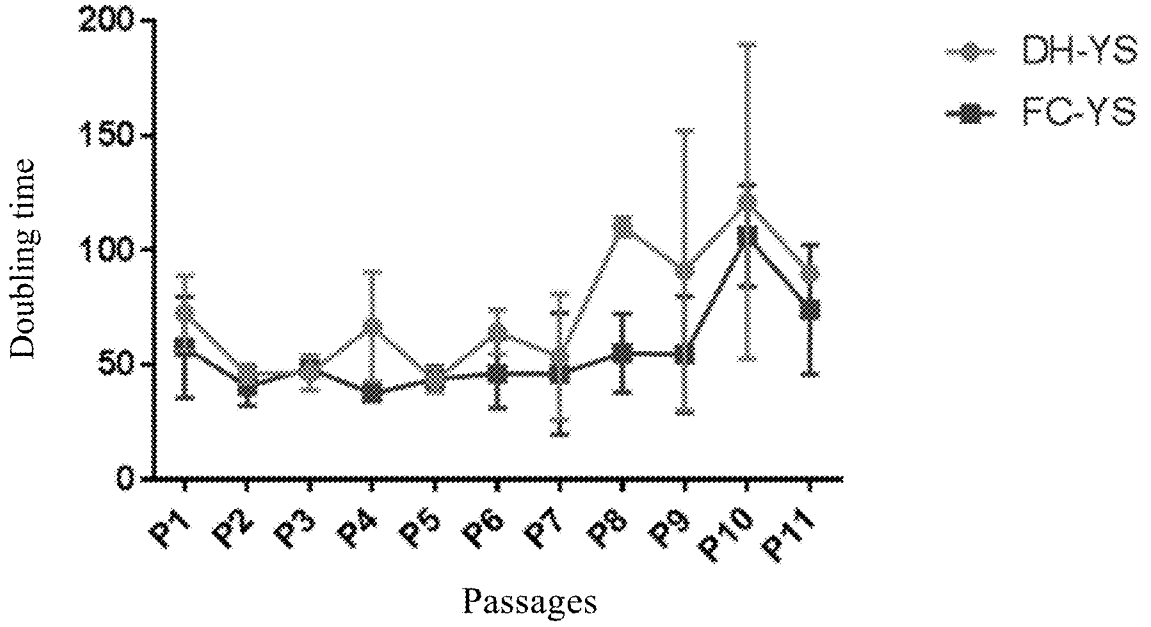
FIG. 2 shows doubling time for EMSCs prepared by the mononuclear method and for EMSCs prepared by the method of the invention in comparison.

IV. Tissue Culturing:

1) The pellet was resuspended in 1 mL medium (Amniocyte Culture Medium, also referred to as "YS" herein below, Guangzhou Baiyunshan Baidi Biopharmaceutical Co., Ltd.). The resuspensions were inoculated into T25 culture flasks, 500 µL/flask, and resuspended by adding 10 mL medium;

2) The cells were mixed by drawing “X” or drawing “8”, and then cultured in an incubator at 37° C., 5% $CO_2$;

3) After culturing for 48 hours, non-adherent contaminant cells (e.g., erythrocytes) were washed off via medium passage, the harvest was quantitated using the AO/PI (AO: Acridine Orange, PI: Propidium Iodide) Double-Stain Apoptosis Detection Kit (a DNA probe-based nuclei double-stain detection, available from Shanghai Ruiyu Biotechnology Co., Ltd.), and fold expansion and doubling time were calculated. The results were as summarized in Table 1 and exhibited in FIGS. 1 and 2.

TABLE 1

Growth Profile of Endometrial Mesenchymal Stem Cells

| Sample No. | Preparation Method | P1 Fold expansion | P1 Doubling Time | P2 Fold expansion | P2 Doubling Time | P3 Fold expansion | P3 Doubling Time | P4 Fold expansion | P4 Doubling Time | P5 Fold expansion | P5 Doubling Time | P6 Fold expansion |
|---|---|---|---|---|---|---|---|---|---|---|---|---|
| 0001 | FC | 7.09 | 50.95 | 13.04 | 38.87 | 7.49 | 49.56 | 14.56 | 37.27 | 9.33 | 37.24 | 7.04 |
| 0031 | FC | 3.36 | 82.36 | 7.44 | 49.74 | 5.17 | 50.63 | 19.49 | 33.61 | 8.29 | 47.19 | 12.16 |
| 0026 | FC | 8.27 | 39.37 | 12.4 | 33.04 | 9.28 | 44.80 | 11.15 | 41.39 | 8.48 | 46.69 | 4.88 |
| 0001 | DH | 5.98 | 55.81 | 7.49 | 49.57 | 8.4 | 46.90 | 11.52 | 40.84 | 6.16 | 45.75 | 3.01 |
| 0031 | DH | 3.09 | 88.47 | 8.4 | 46.90 | 13.28 | 38.59 | 3.12 | 87.72 | 8.37 | 46.98 | 5.44 |
| 0026 | DH | 4.9 | 73.27 | 11.2 | 41.31 | 6.32 | 54.14 | 4.05 | 71.36 | 9.41 | 37.10 | 5.57 |

| Sample No. | P6 Doubling Time | P7 Fold expansion | P7 Doubling Time | P8 Fold expansion | P8 Doubling Time | P9 Fold expansion | P9 Doubling Time | P10 Fold expansion | P10 Doubling Time | P11 Fold expansion | P11 Doubling Time |
|---|---|---|---|---|---|---|---|---|---|---|---|
| 0001 | 42.62 | 8.11 | 31.80 | 4.4 | 44.91 | 3.33 | 82.97 | 13.52 | 25.55 | 1.92 | 102.01 |
| 0031 | 33.30 | 9.44 | 29.64 | 6.29 | 45.23 | 11.7 | 33.78 | 2.27 | 121.80 | 4.32 | 45.48 |
| 0026 | 62.97 | 3.68 | 76.61 | 3.79 | 74.91 | 8.32 | 47.11 | 3.01 | 90.58 | 3.8 | 74.77 |
| 0001 | 75.48 | 7.24 | 25.21 | 1.87 | 106.61 | 3.44 | 53.86 | 2.56 | 88.49 | — | — |
| 0031 | 58.93 | 3.47 | 80.23 | 2.5 | 109.00 | 2.28 | 161.48 | 1.95 | 199.79 | — | — |
| 0026 | 58.12 | 6.13 | 55.05 | 2.384 | 114.89 | 5.6 | 57.94 | 3.79 | 74.91 | 3.04 | 89.77 |

Notes:
1) P1: The first passage of subculturing;
2) FC: The method of the present invention; DH: the mononuclear method.

exchange, and the culturing continues. The cells were ready for passaging when reaching 90% confluence.

Example 2: Growth Profiles of Endometrial Mesenchymal Stem Cells Prepared by Different Methods Endometrial mesenchymal stem cells were prepared using the mononuclear method as described in “Isolation, Culture And Identification Of Menstrual Blood-Derived Mesenchymal stem cells”, Zhou Yun-fang, Yang Bo, Hu Xiang et al., (Chinese Journal of Clinical Rehabilitative Tissue Engineering Research, 2010, 14(32):5952-5956).

An aliquot of the endometrial mesenchymal stem cells prepared in Example 1 and an aliquot of the endometrial mesenchymal stem cells prepared using the mononuclear method were subcultured. Each passage was subcultured via inoculation at a density of $5.0\times10^3$ cells/$cm^2$ into a T75 culture flask containing the Amniocyte Culture Medium (also referred to as “YS”, available from Guangzhou Baiyunshan Baidi Biopharmaceutical Co., Ltd.). At around 90% confluence, the medium was discarded, and the cells were gently washed with phosphate buffer solution (PBS). Then, the washing fluid was discarded and the cells were digested with 3 ml 0.25% trypsin for 4 minutes. 6 ml PBS containing 5% fetal calf serum was added to end the digestion. The cell suspensions were collected into two spin tubes separately, centrifuged at 1500 r/min for 5 min. The supernatants was discarded, and 1 mL Amniocyte Culture Medium (also referred to as “YS”, available from Guangzhou Baiyunshan Baidi Biopharmaceutical Co., Ltd.) was added into each tube to resuspend the cells. For each Results: The mesenchymal stem cells prepared by the method of the invention largely exhibited a higher fold expansion and a reduced doubling time than those prepared by the mononuclear method across passages. Furthermore, the doubling time fluctuated prominently between passages for the MSCs prepared by the mononuclear method while appeared more stable for the MSCs prepared by the method of the invention. Accordingly, the method of the invention is advantageously capable of providing endometrial mesenchymal stem cells with improved doubling time and fold expansion, as compared with the mononuclear method.

Example 3: Differentiation Potency of Endometrial Mesenchymal Stem Cells Prepared by the Method of the Invention Methods: The endometrial mesenchymal stem cells 0031 prepared in Example 1 were plated into wells of a 12-well plate containing the Amniocyte Culture Medium (also referred to as “YS”, available from Guangzhou Baiyunshan Baidi Biopharmaceutical Co., Ltd.) at $1.0\times10^5$ cells/well, and cultured in an incubator at 5% $CO_2$, 37° C. for 3-4 day until reaching 90%-100% confluence. On a clean bench, the medium in each well was aspirated and discarded, then 1 mL/well the Induced Osteogenic Differentiation Complete Medium (available from Cyagen Biotechnology Co., Ltd.) was added. The medium was refreshed every 3 days. At day 21 of the osteogenic differentiation, the cells were stained with Alizarin Red S for osteogenic differentiation. The result was shown in FIG. 3A.

The endometrial mesenchymal stem cells 0031 prepared in Example 1 were resuspended in the Amniocyte Culture Medium at $1.0\times10^7$/ml. The suspension was added evenly in drops onto a 10 $cm^2$ petri dish cover, and incubated in incubator at 5% $CO_2$, 37° C. for 24 hours. On a clean bench, spheric drops were pipetted into wells of a 6-well plate, into which was added 2 mL/well the Chondrogenic Differentiation Medium (available from STEMCELL). The medium was refreshed every 3 days. At day 28 of the chondrogenic differentiation, cell sections were stained with Alcian blue for the chondrogenic differentiation. The result was shown in FIG. 3B.

Figure 3A:
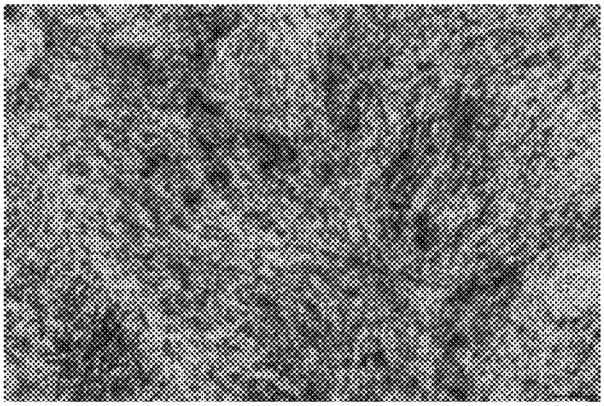
FIG. 3A shows staining of the EMSCs prepared by the method of the invention for osteogenic differentiation potential.
Figure 3B:
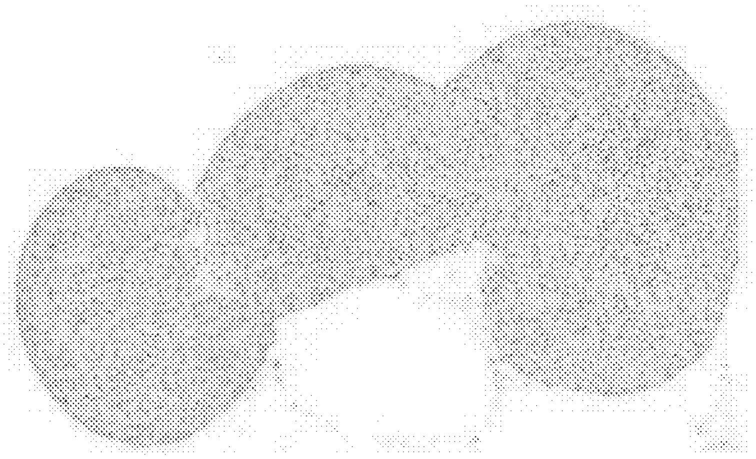
FIG. 3B shows staining of EMSCs prepared by the method of the invention for chondrogenic differentiation potential.

As seen from FIG. 3A, the endometrial mesenchymal stem cells prepared according to Example 1 were prominently visible in orange-red as stained with Alizarin Red S, which indicates a great potential of osteogenic differentiation. As seen from FIG. 3B, the endometrial mesenchymal stem cells prepared according to Example 1 were visible in the tissues in blue as stained with Alcian blue, which indicates the chondrogenic potential. In conclusion, the endometrial mesenchymal stem cells prepared by the method of the invention have sound differentiation potentials.

Despite of the described with specific examples of the invention, it will be apparent to those skilled in the art that various changes and modifications can be made in the present invention without departing from the spirit and scope of the invention, which all fall within the scope of the invention as defined by the appended claims.

What is claimed is:

1. A method for obtaining endometrial mesenchymal stem cells from human menstrual blood, comprising:

1) subjecting an aliquot of menstrual blood to cascade filtration through graded cell strainers of increasing mesh numbers to separate tissue debris, wherein said cell strainers include one or more filter-through cell strainers for collecting filtrate and one or more retention cell strainers for collecting retentate, wherein the mesh number of the one or more retention cell strainers is larger than that of the one or more filter-through strainers;

2) collecting the retentate on the one or more retention cell strainers as the tissue debris;

3) culturing the tissue debris in a mesenchymal stem cells medium to obtain adherent cells; and 4) collecting the adherent cells as the endometrial mesenchymal stem cells;

wherein the one or more retention cell strainers has a mesh number ranging from 70 mesh to 160 mesh, and the one or more filter-through cell strainers has a mesh number ranging from 18 mesh to 60 mesh.

2. The method of claim 1, wherein in said step 1), said cascade filtration includes passing through at least three grades of cell strainers.

3. The method of claim 1, wherein said step 2) of collecting the retentate on the one or more retention cell strainers includes releasing the tissue debris retained on the one or more retention cell strainers via back-flush with a washing fluid.

4. The method of claim 1, wherein said step 2) of collecting the retentate on the one or more retention cell strainers further includes washing the tissue debris with a washing fluid.

5. The method of claim 3, wherein the washing fluid is a phosphate buffer.

6. The method of claim 4, wherein the washing fluid is a phosphate buffer.

7. The method of claim 1, wherein the mesenchymal stem cell medium is selected from the group consisting of MSC primary cell serum-free medium and amniocyte culture medium.

8. The method of claim 1, wherein in step 3), tissue debris is cultured for 4-6 days.

9. The method of claim 1, wherein the one or more retention cell strainers has a mesh number ranging from 80 mesh to 160 mesh.

10. The method of claim 1, wherein the one or more filter-through cell strainers has a mesh number ranging from 36 mesh to 60 mesh.

11. The method of claim 1, wherein the one or more filter-through cell strainers has a mesh number ranging from 36 mesh to 50 mesh.

12. The method of claim 1, wherein the one or more filter-through cell strainers has a mesh number ranging from 36 mesh to 40 mesh.

13. The method of claim 2, wherein the cascade filtration includes passing through at least four grades of cell strainers.

14. The method of claim 2, wherein said cascade filtration includes passing through two or more grades of filter-through cell strainers, two or more grades of retention cell strainers, or both the filter-through and retention cell strainers.

15. The method of claim 2, wherein said cascade filtration includes two or more grades of retention cell strainers, and said step 2) of collecting the retentate on the one or more retention cell strainers includes pooling the tissue debris retained on the two or more grades of retention cell strainers.

16. The method of claim 5, wherein the phosphate buffer comprises an antibiotic.

17. The method of claim 16, wherein the antibiotic is selected from the group consisting of gentamicin, penicillin, streptomycin, amphotericin B, and a combination thereof.

18. The method of claim 17, wherein the concentration of each antibiotic, if present, is selected from: gentamicin at a concentration of 50-100 U/mL, penicillin at a concentration of 180-200 U/mL, streptomycin at a concentration of 0.15-0.2 mg/mL, and amphotericin B at a concentration of 4-5 μg/mL.

19. The method of claim 17, wherein the concentration of each antibiotic, if present, is selected from: gentamicin at a concentration of 100 U/mL, penicillin at a concentration of 200 U/mL, streptomycin at a concentration of 0.2 mg/mL and amphotericin B at a concentration of 5 μg/mL.

20. The method of claim 6, wherein the phosphate buffer comprises an antibiotic.

21. The method of claim 20, wherein the antibiotic is selected from the group consisting of gentamicin, penicillin, streptomycin, amphotericin B, and a combination thereof.

22. The method of claim 21, wherein the concentration of each antibiotic, if present, is selected from: gentamicin at a concentration of 50-100 U/mL, penicillin at a concentration of 180-200 U/mL, streptomycin at a concentration of 0.15-0.2 mg/mL, and amphotericin B at a concentration of 4-5 μg/mL.

23. The method of claim 21, wherein the concentration of each antibiotic, if present, is selected from: gentamicin at a concentration of 100 U/mL, penicillin at a concentration of 200 U/mL, streptomycin at a concentration of 0.2 mg/mL and amphotericin B at a concentration of 5 μg/mL.

24. The method of claim 8, wherein the tissue debris is cultured for 5 days.

* * * * *